(12) United States Patent    (10) Patent No.: US 7,129,509 B2
Katzir et al.                (45) Date of Patent: Oct. 31, 2006

(54) HIGH-SENSITIVITY OPTICAL SCANNING USING MEMORY INTEGRATION

(75) Inventors: Yigal Katzir, Rishon Lezion (IL); Itay Gur-Arie, Rishon Lezion (IL); Yacov Malinovich, Kiriat Tivon (IL)

(73) Assignee: Orbotech, Ltd., Yavne (IL)

( * ) Notice: Subject to any disclaimer, the term of this patent is extended or adjusted under 35 U.S.C. 154(b) by 0 days.

(21) Appl. No.: 11/225,041

(22) Filed: Sep. 14, 2005

(65) Prior Publication Data

US 2006/0006311 A1    Jan. 12, 2006

Related U.S. Application Data

(63) Continuation of application No. 10/176,003, filed on Jun. 21, 2002.

(60) Provisional application No. 60/299,766, filed on Jun. 22, 2001.

(51) Int. Cl.
G01N 21/88 (2006.01)
H01L 27/00 (2006.01)

(52) U.S. Cl. .............. 250/559.45; 250/208.1; 348/125; 348/295

(58) Field of Classification Search .......... 250/208.1, 250/559.45; 348/295, 319, 321, 125–126; 382/92, 584, 588, 598, 88, 601; 345/629, 345/634, 638–640, 643
See application file for complete search history.

(56) References Cited

U.S. PATENT DOCUMENTS

| 4,949,172 A | 8/1990 | Hunt et al. |
|---|---|---|
| 5,040,057 A | 8/1991 | Gilblom et al. |
| 5,264,912 A | 11/1993 | Vaught et al. |
| 5,440,648 A | 8/1995 | Roberts et al. |
| 5,461,425 A | 10/1995 | Fowler et al. |
| 5,471,515 A | 11/1995 | Fossum et al. |
| 5,488,415 A | 1/1996 | Uno |
| 5,668,887 A * | 9/1997 | Parker et al. ............... 382/108 |
| 5,717,780 A * | 2/1998 | Mitsumune et al. ........ 382/141 |
| 5,750,985 A | 5/1998 | Suzuki |
| 5,812,190 A | 9/1998 | Audier et al. |
| 5,812,704 A * | 9/1998 | Pearson et al. ............. 382/284 |
| 5,841,126 A | 11/1998 | Fossum et al. |
| RE36,047 E | 1/1999 | Gilblom et al. |
| 5,909,026 A | 6/1999 | Zhou et al. |
| 6,005,617 A | 12/1999 | Shimamoto et al. |
| 6,020,957 A | 2/2000 | Rosengaus et al. |
| 6,057,539 A | 5/2000 | Zhou et al. |
| 6,069,365 A | 5/2000 | Chow et al. |
| 6,115,066 A | 9/2000 | Gowda et al. |
| 6,169,600 B1 | 1/2001 | Ludlow |

(Continued)

FOREIGN PATENT DOCUMENTS

EP    0 543 629 A1    5/1993

(Continued)

OTHER PUBLICATIONS

Kleinfelder et al., "A 10,000 Frame/s 0.18 μm CMOS Digital Pixel Sensor with pixel-Level Memory", 2001 International Solid State Circuits Conference, Feb. 5, 2001.

(Continued)

Primary Examiner—Stephone B. Allen
Assistant Examiner—Patrick J. Lee
(74) Attorney, Agent, or Firm—Sughrue Mion, PLLC

(57) ABSTRACT

An inspection system includes a CMOS integrated circuit having integrally formed thereon an at least two dimensional array of photosensors and providing an inspection output representing an object to be inspected. A defect analyzer is operative to receive the inspection output and to provide a defect report.

56 Claims, 15 Drawing Sheets

U.S. PATENT DOCUMENTS

| | | |
|---|---|---|
| 2001/0012069 A1 | 8/2001 | Demdinger et al. |
| 2001/0021244 A1 | 9/2001 | Suzuki et al. |
| 2002/0145112 A1 | 10/2002 | Davidson |
| 2002/0186878 A1* | 12/2002 | Hoon et al. ................. 382/149 |

FOREIGN PATENT DOCUMENTS

| | | |
|---|---|---|
| EP | 0 738 886 A2 | 10/1996 |
| EP | 0 796 005 A2 | 9/1997 |
| WO | WO 97/33159 A1 | 9/1997 |
| WO | WO 00/42381 A1 | 7/2000 |

OTHER PUBLICATIONS

Pain et al., "CMOS Image Sensors Capagble of Time-Delayed Integration", NASA Tech Brief vol. 25, No. 4, Apr. 1, 2001.

* cited by examiner

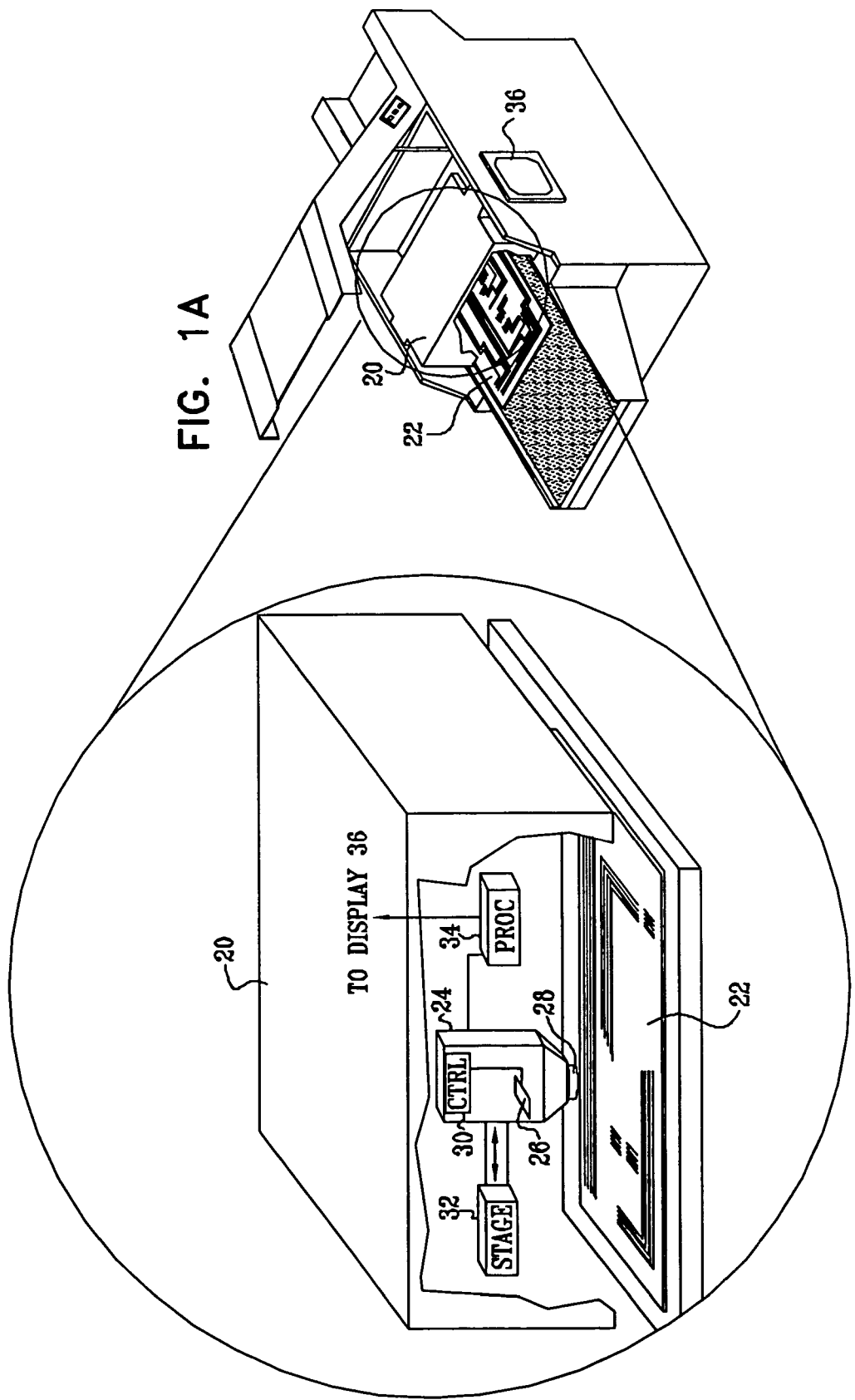

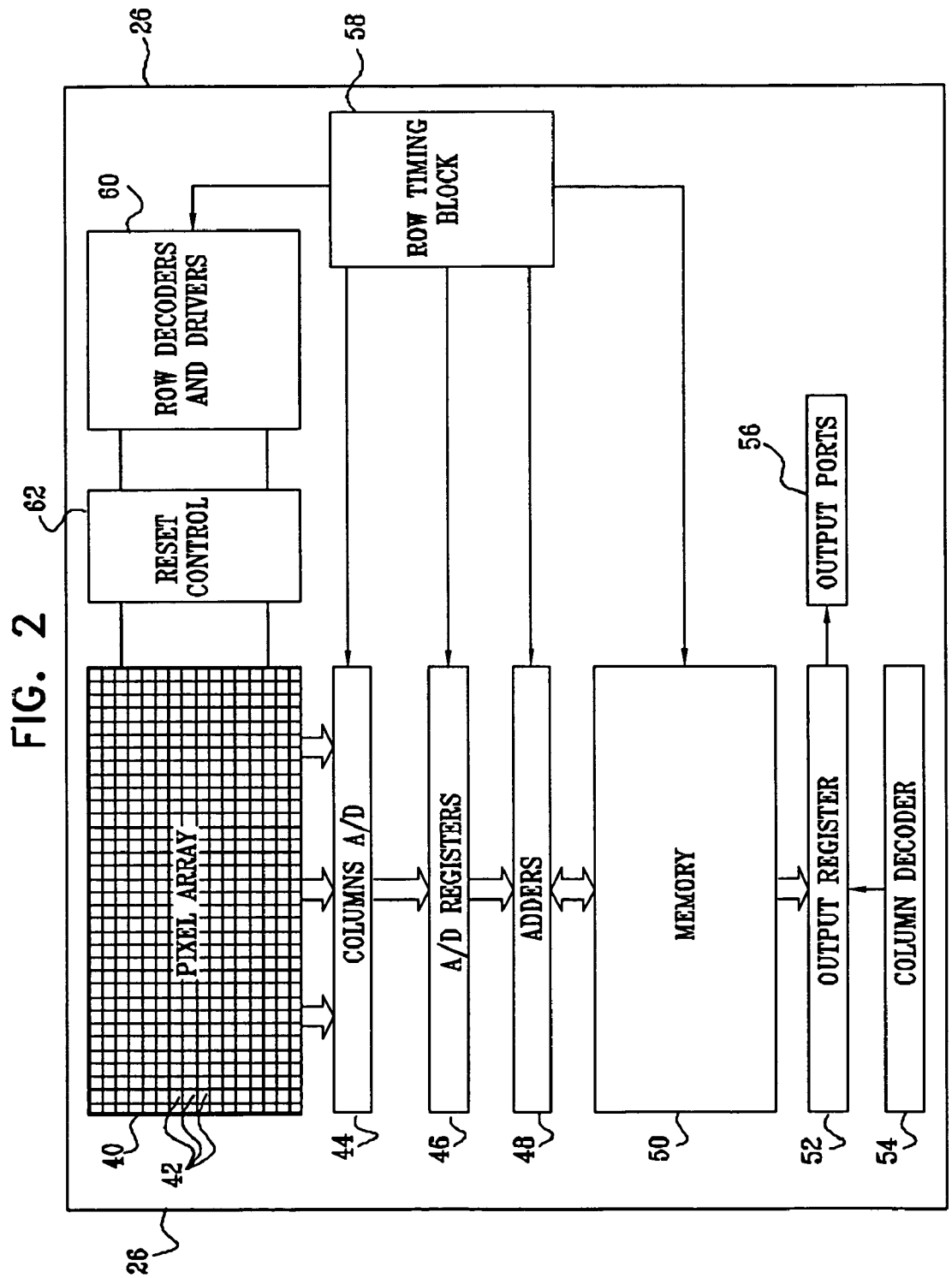

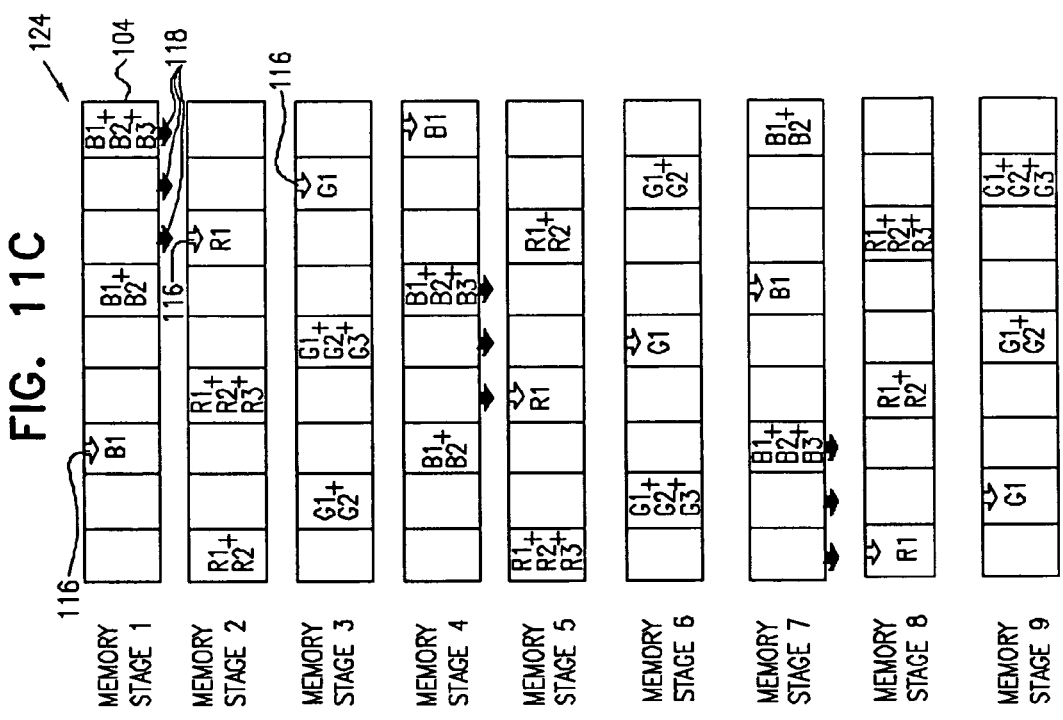
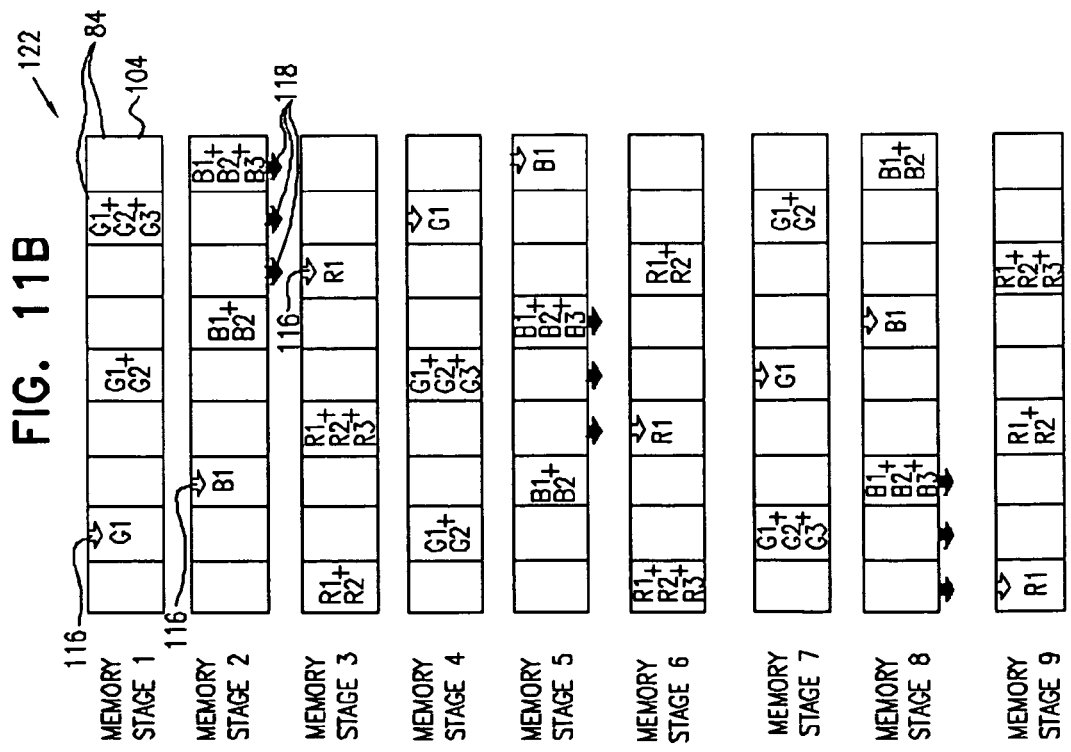

HIGH-SENSITIVITY OPTICAL SCANNING USING MEMORY INTEGRATION

CROSS-REFERENCE TO RELATED APPLICATION

This is a continuation of application Ser. No. 10/176,003 filed Jun. 21, 2002, which claims the benefit of U.S. Provisional Patent Application No. 60/299,766, filed Jun. 22, 2001, both of which are hereby incorporated by reference.

FIELD OF THE INVENTION

The present invention relates generally to optical scanning systems and sensors, and specifically to scanning techniques employing two dimensional sensor arrays.

BACKGROUND OF THE INVENTION

Scanner systems for acquiring an image of an object, such as a printed circuit board, are well known in the arts of imaging and automated optical inspection. Some conventional scanner systems include sensors comprising a linear array of sensor elements. Other conventional scanner systems include sensors comprising a two dimensional array of sensor elements. Some systems employing two-dimensional array of sensor elements have been configured, for example, to operate in a time delay integration (TDI) mode of operation to acquire and image of an object. Other system employing a two-dimensional array of sensor elements have been configured to acquire a sequence of non overlapping images of an object.

TDI systems are well known in the art of optical scanning. In such systems, a sensor array is scanned over an object, such as a printed circuit board, by moving either the array or the object in a direction perpendicular to the rows of the array. The scanning speed and an array clock are synchronized so that in each column of the array, multiple sensor elements in sequence capture light from the same point on the object. Charge is accumulated between rows as the sensor array passes over the object so that sensor signals in each column are summed for each point on the object, thereby providing an image of the object with enhanced signal/noise ratio.

Common TDI sensors are based on charge-coupled device (CCD) technology, which allows the sensor signals to be summed by transferring charge along each column of the sensory array such that newly accumulated charge is added to charge having accumulated in previous rows of the column. Other TDI systems based on photodiode arrays, such as CMOS sensor arrays, are also known in the art.

U.S. Pat. Nos. 5,750,985 and 5,909,026, the disclosures of which are incorporated by reference, both describe sensors that can be employed in a TDI type arrangement.

Applicants' copending U.S. patent application Ser. No. 10/141,988, filed on May 10, 2002 and entitled "Optical Inspection System Employing a Staring Array Scanner", the disclosure of which is incorporated by reference, describes an inspection system employing a two dimensional sensor array.

SUMMARY OF THE INVENTION

It is an object of some aspects of the present invention to provide improved systems and methods for automated optical inspection (AOI).

It is a further object of some aspects of the present invention to provide improved imaging techniques and devices employing two dimensional sensors.

In accordance with a broad aspect of the present invention, an at least two dimensional array of photosensors formed on a CMOS integrated circuit is employed to acquire images representing an object, such as images of an electrical circuit. At least partially overlapping images are acquired, and pixels in the overlapping images, associated with corresponding portions of the object, are added together to form a composite image of the object. The composite image is particularly useful, for example, to inspect the object for defects. As used herein the term CMOS integrated circuit generally includes any suitable integrated circuit comprising photosensors, such as photodiodes or photogates, other than CCD type photosensors.

In preferred embodiments of the present invention, a two-dimensional imaging device comprises a two-dimensional sensor array and a memory, having cells arranged in rows and columns that correspond to the rows and columns of sensor elements in the array. The array and memory are configured to operate in a memory integration mode so as to provide a composite image as the array scans over an object. In each cycle of the array clock (i.e., each time the sensor array captures an image frame), the signal received by each of the sensor elements is digitized and added to the value stored in one of the cells of the memory. A dynamic input pointer indicates, for each row of the sensor array, the row in the memory into which the signals from the sensor elements in that row of the array should be added. The input pointer is advanced at each cycle of the array clock in such a way that each memory cell receives a sum of signals from multiple sensors in the same column of the array, captured as the sensors pass over the same point on the object. A dynamic output pointer is also updated at each cycle to indicate the row of the memory in which integration has been completed, so that the memory integrated signal can be read out.

This use of dynamic input and output pointers enables the sensor array, memory and memory integration logic to be efficiently implemented together on a single chip, preferably using active pixel CMOS sensor elements. The dynamic pointer scheme also allows the direction of scanning the array to be reversed simply by reversing the pointer direction, so that the object can be scanned in a bidirectional serpentine pattern, for example. This feature is particularly useful in AOI systems.

In some preferred embodiments of the present invention, the sensor array comprises color filters, so that the memory integrated image captured by the array and memory comprises a color image. Preferably, the color filters are arranged so that successive rows of the array receive light of different colors, typically in a repeating red-green-blue pattern. Alternatively, the color filters may be arranged so that successive groups of rows receive light of different colors, for example, several red rows, followed by several green rows, followed by several blue rows. Dynamic input and output pointers are provided for each color. The dynamic pointer configuration and scan rate of the array over the object may be chosen to give either a color memory integrated image with full resolution, equal to that of a comparable monochrome memory integrated image, or a color memory integrated image that has reduced resolution, but whose throughput (i.e., speed of image capture) is equal to that of a monochrome memory integrated image.

In some preferred embodiments of the present invention, the two dimensional imager is used in an AOI system, typically for evaluating characteristics of objects such as printed circuit boards, flat panel displays, electronic assembly boards, and the like. The features of the memory integrated imager described above enable the system to operate at high speed and with high sensitivity, in either a monochrome or color imaging mode.

The present invention will be more fully understood from the following detailed description of the preferred embodiments thereof, taken together with the drawings in which:

BRIEF DESCRIPTION OF THE DRAWINGS

FIG. 1A is a schematic, pictorial illustration of a system for automated optical inspection (AOI), in accordance with a preferred embodiment of the present invention;

FIG. 2 is a block diagram that schematically illustrates a two dimensional imaging device, in accordance with a preferred embodiment of the present invention;

FIGS. 11B and 11C are block diagrams that schematically illustrate contents of memory cells in the imaging device of FIG. 11A.

DETAILED DESCRIPTION OF PREFERRED EMBODIMENTS

Figure 1B:
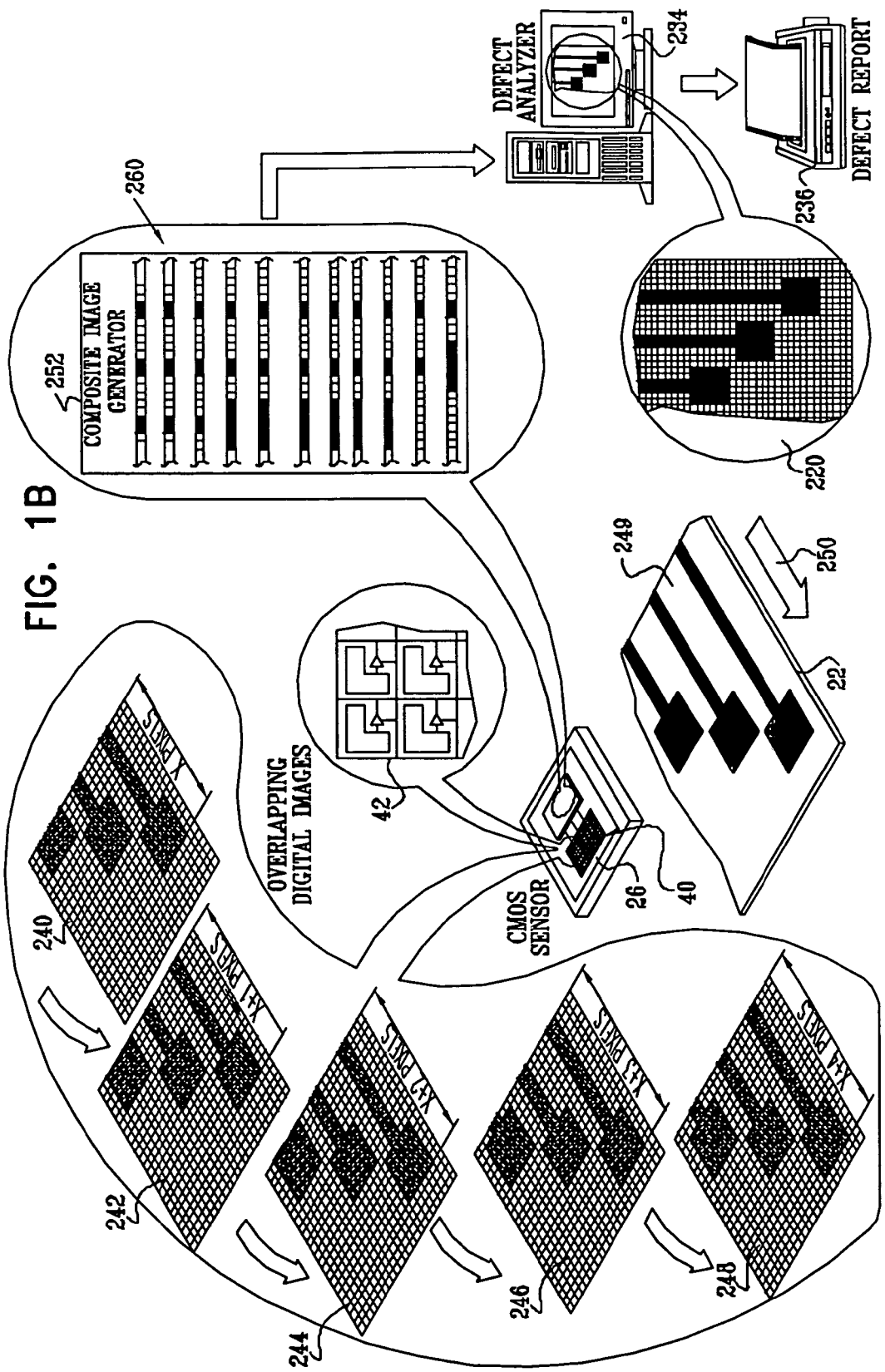
FIG. 1B is a simplified pictorial illustration that generally shows the operation of the system of FIG. 1B in accordance with a preferred embodiment of the present invention.

FIG. 1A is a schematic, pictorial illustration of a system 20 for automated optical inspection (AOI) of a printed circuit board 22, in accordance with a preferred embodiment of the present invention. Board 22 is shown here by way of example, and system 20 may similarly be adapted for inspection of other objects, such as flat panel displays, printed circuit boards loaded with electronic components, integrated circuits, interconnect devices and moving webs. As used herein, the term electrical circuit or board shall generally include any such suitable article to be inspected. The principles of the present invention, as described in greater detail hereinbelow, may also be applied in other areas of digital imaging, such as aerial surveillance.

System 20 captures images of board 22 using a camera 24, which is built around a CMOS integrated circuit imaging device 26 having an at least two dimensional array of photosensors integrally formed thereon. In accordance with an embodiment of the invention, imaging device 26 is operational in a memory integration mode of operation. An objective lens 28 forms an image of board 22 on device 26 as camera 24 is scanned over the surface of the board by a translation stage 32. Preferably, the camera is scanned over the surface in a bidirectional serpentine pattern, so that the entire surface is imaged by the camera at a desired level of resolution. Alternatively, board 22 may be translated while holding camera 24 still, or both the board and camera may be translated, typically in mutually-perpendicular directions. A light source (not shown) illuminates board 22 as it is imaged by camera 24, preferably by providing generally continuous illumination, or by providing non-continuous illumination that is generally synchronized with a frame rate of image frames acquired by imaging device 26.

A camera control unit 30 regulates the timing and operation of device 26, and passes image data from device 26 to an image processor, or analyzer, 34. The image processor analyzes the image data to locate and identify faults, or defects, in board 22. In accordance with a preferred embodiment of the invention processor 34 comprises combinations of image processing hardware and software such as are used in various AOI systems available from Orbotech Ltd. of Yavne, Israel, including the Inspire 9060™ and SK-75™ AOI systems. Alternatively or additionally, processor 34 may comprise a general-purpose computer with suitable input circuits and software for this purpose, hard-wired logic and/or a programmable digital signal processor. For each board tested by system 20, processor 34 outputs either a notification that the board is acceptable or an indication (such as a map) of a fault or faults found in the board, via a display 36 or other output interface.

Figure 1C:
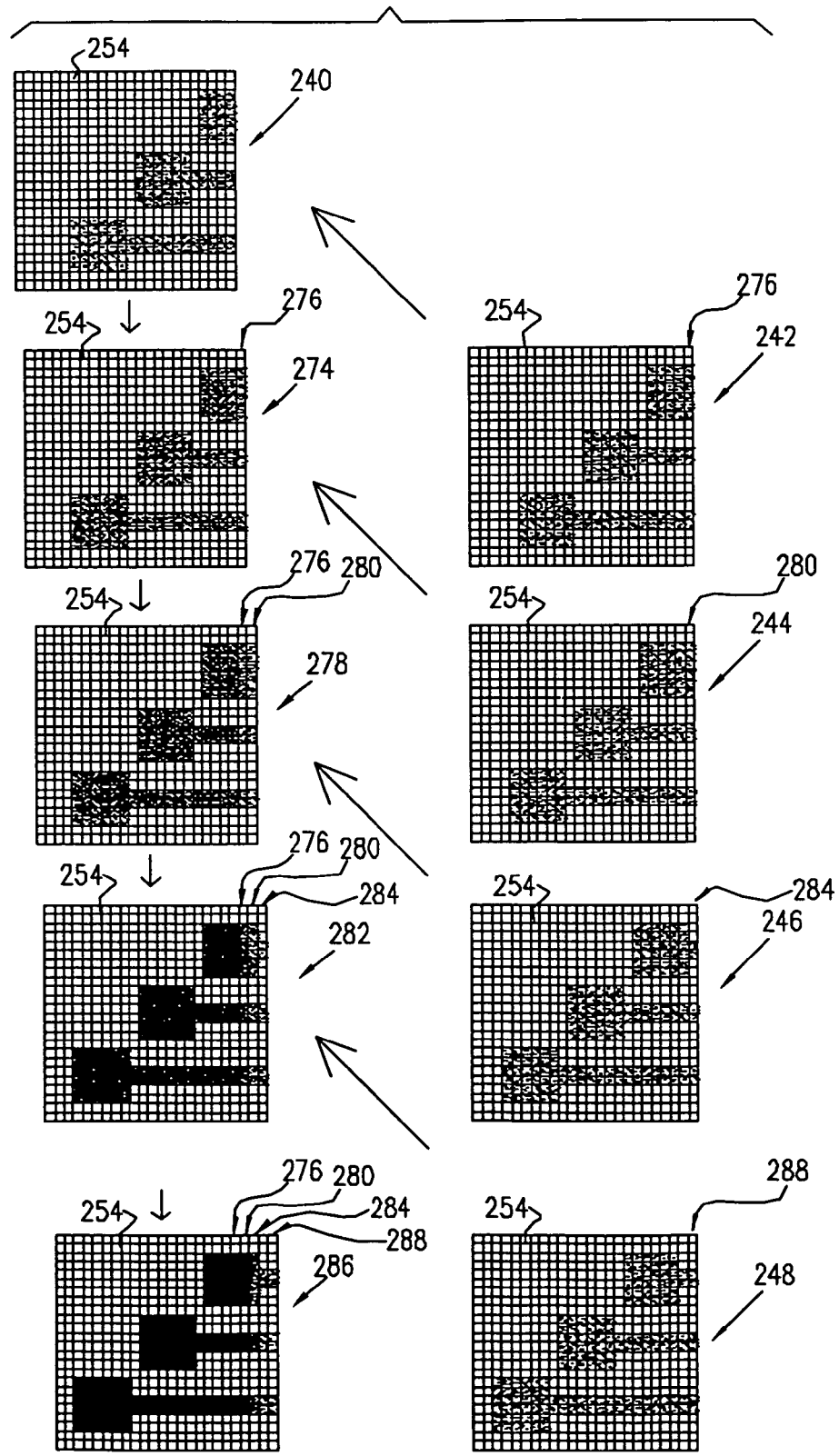
FIG. 1C is more detailed illustration showing operation of a composite image generator shown in FIG. 1B.

FIG. 1B is a simplified pictorial illustration that generally shows the operation of system 20, in accordance with a preferred embodiment of the present invention, and to FIG. 1C which is a more detailed illustration showing operation of a composite image generator seen in FIG. 1B. Imaging device 26 comprises an at least two dimensional array 40 of photosensors 42 integrally formed on a CMOS integrated circuit. Imaging device 26 generates an inspection output, typically in the form of image data 220, which corresponds to an object to be inspected such as board 22. Defect analyzer 234 receives the image data from imaging device 26 and provides a defect report 236 reporting defects on board 22, in response to analyzing the image data 220.

As seen in FIG. 1B, imaging device 26 is operative to acquire a plurality of images of board 22 during the scanning thereof. Five representative of sequentially acquired images, designated 240, 242, 244, 246 and 248 respectively, are seen in FIG. 1B.

In accordance with an embodiment of the invention, images 240–248 are digital pixel images that are sequentially acquired by imaging device 26 during scanning a portion of board 22. Only five images are shown for the sake of simplicity. Typically a much greater number of images is acquired. Each of the images 240–248 corresponds to a mutually offset portion of board 22 such that each image of board 22 acquired by imaging device 26 at least partially overlaps another image. The mutual offset between images may be as small as 1 pixel, although the mutual offset between images may be greater.

Thus, as seen in FIG. 1B, image 240 is acquired by imaging device 26 in a first image frame. After board 22 advances relative to imaging device 26 in the direction of arrow 250 by a distance of 1 pixel, image 242 is acquired in a second image frame. After board 22 further advances relative to imaging device 26 in the direction of arrow 250 by a distance of 1 pixel, image 244 is acquired in a third frame. After board 22 further advances relative to imaging device 26 in the direction of arrow 250 by a distance of 1 pixel, image 246 is acquired in a fourth frame. After board 22 further advances relative to imaging device 26 in the direction of arrow 250 by a distance of 1 pixel, image 248 is acquired in a fifth frame. This sequence continues until at least partially overlapping images are acquired for an entire portion of board 22.

A composite image generator 252 is operative to combine together each of the partially overlapping images generated by array 40, for example images 240–248, and to supply composite image data 260 to analyzer 234. The composite image data 260 forms image 220 which has an improved signal/noise ratio compared to images 240–248. Image 220 is used by defect analyzer 234 to detect defects in board 22.

In accordance with an embodiment of the invention, composite image generator 252 is integrally formed on imaging device 26, although this need not be the case. As seen in FIG. 1B, each of images 240–248 is a relatively weak image of board 22, while image 220, which is the result of combining images 240–248 comprises a significantly stronger image, as seen by the enhanced darkness of image portions corresponding to conductors 249.

The operation of composite image generator may be better understood from FIG. 1C. Corresponding pixels 254 in each of images 240–248 are added together to enhance pixel strength, that is to say improve signal to noise. Pixels 254 in image 242 are added to corresponding pixels 254 in image 240 to result in first composite image 274. It is seen that image 242 is offset relative to image 240 and includes a sequentially added row of pixels 276. It is noted that for reasons of simplicity of presentation, due to orientation of images in FIG. 1C, the rows are actually seen as being columns. Pixels 254 to the left of row 276 in first composite image 274 are darker than pixels in row 276.

Pixels in image 244 are added to corresponding pixels in first composite image 274 to result in second composite image 278. It is seen that image 244 is offset relative to first composite image 274 and includes a sequentially added row of pixels 280. Pixels to the left of row 276 in second composite image 278 are darker than pixels in row 276, and pixels in row 276 are darker than pixels in row 280.

Pixels in image 246 are added to corresponding pixels in second composite image 278 to result in third composite image 282. It is seen that image 246 is offset relative to second composite image 278 and includes a sequentially added row of pixels 284. Pixels to the left of row 276 in third composite image 282 are darker than pixels in row 276, pixels in row 276 are darker than pixels in row 280, and pixels in row 280 are darker than pixels in row 284.

Pixels in image 248 are added to corresponding pixels in third composite image 282 to result in fourth composite image 286. It is seen that image 248 is offset relative to third composite image 282 and includes a sequentially added row of pixels 288. Pixels to the left of row 276 in fourth composite image 286 are darker than pixels in row 276, pixels in row 276 are darker than pixels in row 280, pixels in row 280 are darker than pixels in row 284, and pixels in row 284 are darker than pixels in row 288.

The above process is continued sequentially until a desired quantity of corresponding pixels are added together such that a gradient is formed in the composite image. At the end of each frame, line of pixels comprising the result of adding together a plurality of pixels, is provided as image data 260 (FIG. 1B).

It is a feature of some embodiments of the present invention that values added together in the respective images 240–248 are digital values. The digital values are provided by at least one A/D converter associated with photosensors 42. An A/D converter may be associated with each photosensor 42. Optionally, each A/D converter is associated with a plurality of photosensors 42. For example, each A/D converter is associated with a row of photosensors.

Preferred embodiments of the architecture, functionality and operation of imaging device 26 will be discussed hereinbelow in greater detail. In general, it is noted that imaging device 26 includes a plurality of digital registers which are operative to temporarily store the outputs of the A/D converters, digital memory, typically including an array of memory cells, storing image data provided by the array of photosensors, and a plurality of digital adders operative to add the outputs of the digital registers to corresponding image data which is stored in the digital memory.

Moreover, in accordance with embodiments of the invention the adding together of images, such as images 240–248, is performed on the fly on a line by line basis, and composite images are stored in a memory array in a wrap-around manner that dynamically changes as each new image 240–248 is acquired and added to a previously stored composite image.

It is noted that images 240–248 seen in FIG. 1B generally correspond to images formed on array 40. Typically these images are not stored between the acquisition of successive image frames. As will be appreciated from the following detailed discussion of the operation of imaging device 26, each line in images 240–248 is retrieved and added to a corresponding line in a previously stored composite image, as described with reference to FIG. 1C.

FIG. 2 is a block diagram that schematically shows the structure of a memory integration imaging device 26, in accordance with a preferred embodiment of the present invention. Device 26 is preferably fabricated as a single integrated circuit (IC) chip, most preferably using a CMOS process. A sensor array 40 comprises a two-dimensional matrix of sensor elements 42, preferably active pixel sensors. In each frame (i.e., at each cycle of the array clock), each element 42 generates a signal proportional to the light intensity incident thereon. The signals are typically read out from the sensor array via column decoder 54 and digitized by an array 44 of A/D (analog to digital) converters and are then stored temporarily in an array 46 of registers, with one register per column of sensor array 40. Alternatively, sensor elements 42 may comprise digital pixel sensors, as described, for example, by Kleinfelder et al., in "A 10,000 Frames/s 0.18 μm CMOS Digital Pixel Sensor with Pixel-level Memory," presented at ISSCC 2001, which is incorporated herein by reference. In this case, the output of array 40 is already digitized, and A/D converters 44 are unnecessary.

The digitized signal values held in register array 46 are summed by an array 48 of adders with corresponding stored values in rows of a memory 50, which typically comprises high-speed static or dynamic random access memory (SRAM or DRAM) or any other suitable type of memory. The results of the summation are stored back in the same row of the memory. This read/sum/store operation is typically performed for each cell in memory 50 once per frame. It is repeated over a predetermined number of frames, each time adding in the signal from a different row in array 40, until the memory cell contains the sum of the signals taken from the predetermined number of different elements 42 in the same column of the array. The association of sensor elements with memory cells at each cycle is controlled by a system of dynamic pointers, as described below. After the required number of summations of values from different elements 42 have been performed for a given row of memory 50, the results in that row are read out to an array 52 of output registers. These data are then clocked out of the registers to output ports 56 via a column decoder 54, for readout to processor 34.

In a preferred embodiment of the invention, as seen in FIG. 2, a row timing block 58 is responsible for maintaining synchronization of the image frame capture and readout by array 40, along with the corresponding operations of A/D converter array 44, register array 46, adder array 48 and memory 50. The row timing is synchronized with the speed of scanning camera 24 over board 22, as described below, such that those values from elements 42 that are added together at adders 48 generally correspond to the same location on a board 22. Block 58 controls the location of the dynamic pointers used in selecting the rows of memory 50 for adding and readout and also includes the memory row decoder, in order to achieve a desired effect. Block 58 also controls row decoders and drivers 60, for reading out the signals from elements 42 row by row in each frame, and for resetting array 40 at the end of each frame, via a reset control block 62.

Figure 3:
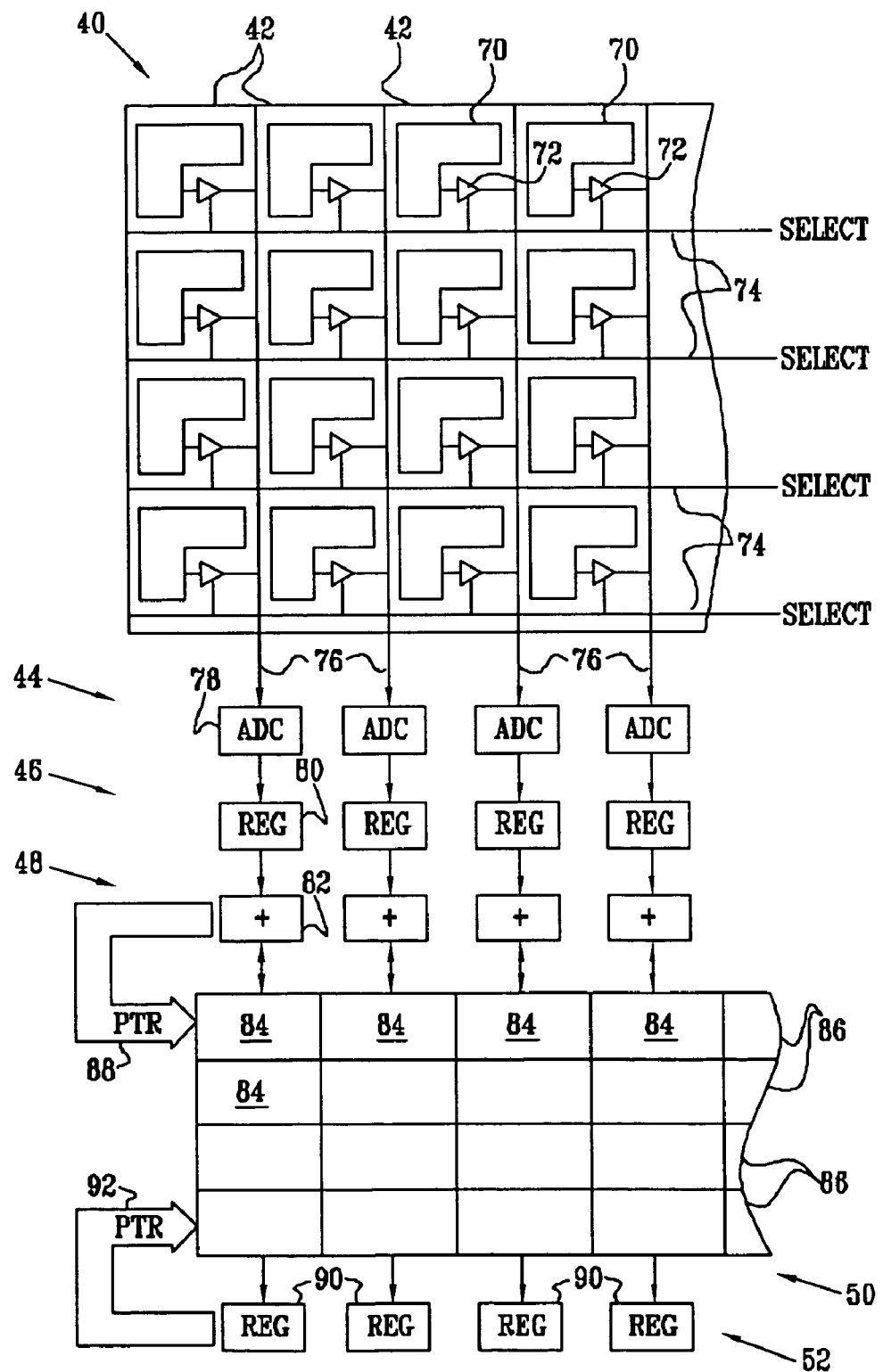
FIG. 3 is a block diagram that schematically shows details of the imaging device of FIG. 2, in accordance with a preferred embodiment of the present invention.

FIG. 3 is a block diagram showing details of device 26, in accordance with a preferred embodiment of the present invention. In this simplified embodiment, it is assumed that array 40 and memory 50 each comprise four rows. For each column in array 40, there is a corresponding column of cells in memory 50. For simplicity, only four of these columns are shown, as well.

Each sensor element 42 comprises a photodetector (or photosensor) 70, typically a photodiode or photogate, and an active amplifier 72 which also includes, for example, a select transistor (not shown). The amplifiers are triggered by row select lines 74 to read out the charge stored by the corresponding photodetectors to column output lines 76. Photodetectors 70 are preferably designed for low capacitance, in order to reduce the level of reset thermal (kTC) noise that they generate. In accordance with a preferred embodiment, each pixel also comprises a reset circuitry (not shown), which is separately controlled by reset control 62. Optionally, each sensor element may comprise a separate charge storage element, such as a capacitor (not shown), to which charge is transferred from the photodetector and held until it is read out of the array. As a further option, mentioned above, each sensor element may comprise a built-in A/D converter (not shown). Other means known in the art may also be used to enhance the sensitivity and signal/noise ratio of array 40, such as the use of microlenses, integrated with the array, to focus light received by camera 24 onto photodetector 70 within each sensor element 42.

Preferably, A/D converter array 44 comprises one A/D converter 78 per column of array 40. Optionally, an A/D converter may be associated with each element 42. At each cycle of the row clock generated by row timing block 58, converter 78 digitizes the signal from a successive element 42 in its corresponding column of array 40. The digitized value is held in a register 80 in register array 46, until it is summed by an adder 82 with the contents of a selected cell 84 in memory 50. The sums output by adders 82 are written back to the same cells in memory 50 from which the addends were read out. Memory cells 84 are arranged in columns corresponding to the columns of sensor elements 42 in array 40. In the present embodiment, cells 84 are arranged in four rows 86, corresponding to the four rows of elements 42 in array 40. The row whose cells 84 are to be read out for summing by adders 82 at each cycle of the row clock is determined by an input pointer 88. After a complete frame has been read out of array 40, digitized and summed into the appropriate cells in memory 50, pointer 88 is advanced to a new position for the next frame. As a result, each cell 84 in memory 50 receives the sum of the signals generated by all four sensor elements 42 in the corresponding column of array 40.

An output pointer 92 is used to indicate the row 86 in memory 50 whose cells 84 contain the summed signals from all four of the sensor elements 42 in the corresponding column of array 40. At each cycle of the row clock, the contents of these cells are read out to registers 90 in output register array 52. After the contents of a row of cells have been read out, the cells are reset to zero. Then, during the next frame, input pointer 88 is advanced so that the null contents of these memory cells are summed with the signals from the sensor elements in the first row of sensor array 40. In each subsequent frame, the pointers are advanced, and summations are performed, until the cells again contain the sum of signals from all four rows of the sensor array and can again be read out. Output pointer 92 is likewise advanced in each frame to point to the next row of memory 50 that is to be read out.

Figure 4:
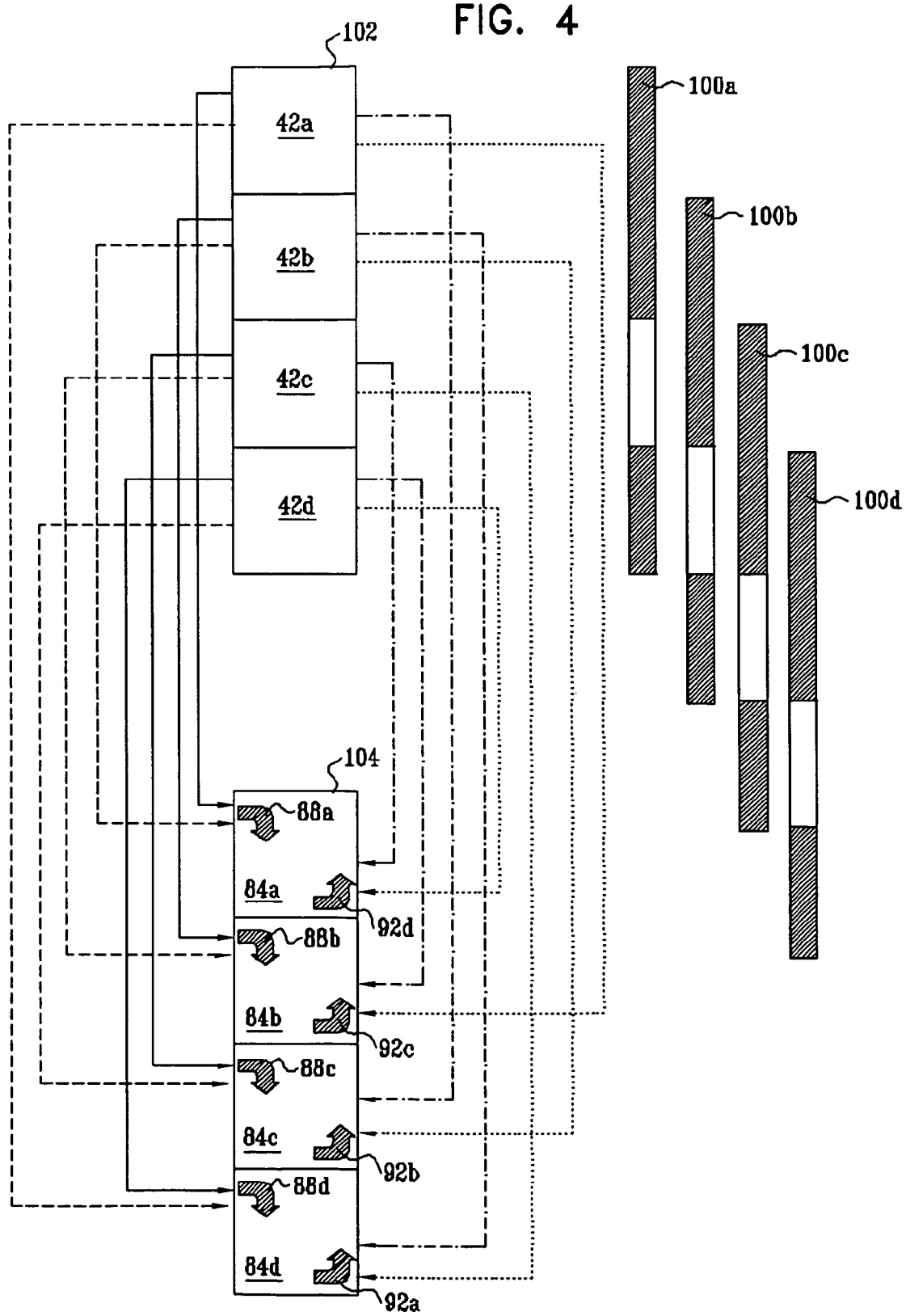
FIG. 4 is a block diagram that schematically illustrates the use of memory pointers in the imaging device of FIG. 2, in accordance with a preferred embodiment of the present invention.

FIG. 4 is a block diagram that schematically shows a single column 102 of sensor array 40, and a single column 104 of memory 50, illustrating the use of pointers 88 and 92, in accordance with a preferred embodiment of the present invention. In the embodiment shown in the preceding figures, all columns are treated identically, so that the example shown here in FIG. 4 is representative of the handling of the entire array. An arbitrary object 100 is imaged onto column 102 of array 40 in four successive frames, designated a–d respectively. For clarity of illustration, the object is shown alongside column 102, rather than superimposed on it. The position of the object, which is in a translated location respective of column 102 in each of four successive frames of array 40, is shown by successive bars 100a, 100b, 100c and 100d. It will thus be observed that the array clock of array 40 is synchronized with the speed of scanning the array over the object (or moving the object under the array), so that the object advances by one pixel in each successive frame. In other words, a point on object 100 that is imaged onto sensor element 42a in the first frame is imaged onto the next sensor element 42b in the second frame, and so forth up to element 42d.

Input pointer 88 is set in each frame to point to the cell 84 in memory 50 to which the signal from sensor element 42a is to be added. The location of the input pointer in each of the four successive frames (corresponding to bars 100a–d) is shown in FIG. 4 by pointers 88a, 88b, 88c and 88d, respectively. The signals from elements 42b, 42c and 42d are written to the succeeding cells in column 104, wrapping around back to the top of the column when the last cell (84d) is reached. The correspondence between sensor elements 42 and memory cells 84 in each of the four successive frames is indicated by solid arrows for the first frame (bar 100a), dashed arrows in the second frame (bar 100b), dash-dot arrows in the third frame (bar 100c), and dotted arrows in the fourth frame (bar 100d).

Output pointer 92 is set in each frame to point to the cell 84 in memory 50 to which the signal from sensor element 42*d* is added. This cell will contain, after the output of sensor 82 is written back to the cell, the sum of the signals from all four of sensor elements 42*a*–42*d* in column 102 for each successive pixel on object 100. The contents of this cell can thus be read out to register 90 and then reset to zero. The position of the output pointer in each of the four successive frames is shown in FIG. 4 by pointers 92*a*, 92*b*, 92*c* and 92*d*, respectively. When output pointer 92 points to a given cell in one frame, input pointer 88 will point to that same cell in the next frame. Thus, on the next cycle of the array clock, the cell will begin to accumulate image data from sensor element 42*a* captured from a new pixel on the object.

Figure 5:
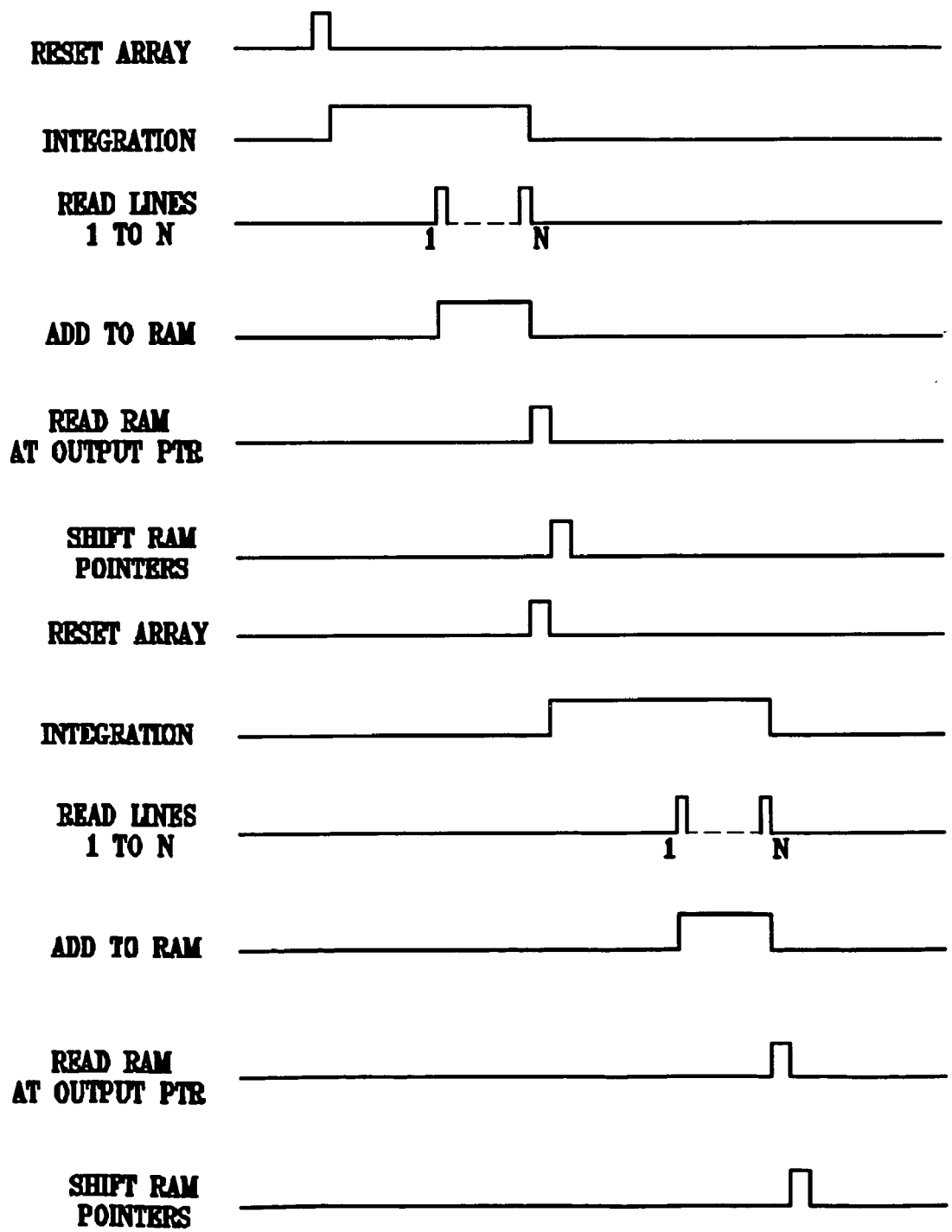
FIGS. 5–8 are timing diagrams that schematically illustrate the operation of the device of FIG. 2, in accordance with preferred embodiments of the present invention.

FIG. 5 is a timing diagram that schematically shows timing signals associated with the operation of imaging device 26, in accordance with a preferred embodiment of the present invention. The figure illustrates the operation of the device over two cycles of the array clock, i.e., two frames. Each frame begins by resetting sensor array 40, to remove residual charge from sensor elements 42, and then allowing the sensor elements to integrate charge over the remainder of the frame. The signals generated by the sensor elements are read out of array 40 row by row, for rows 1 through N of the array. The signal values are digitized and summed into memory 50, as described above.

After all the summations are complete, the summed data are read out of cells 84 in the row 86 of memory 50 that is indicated by output pointer 92. Pointers 88 and 92 are then advanced to their positions for the next frame. As soon as all the rows of array 40 have been read out (even before the pointers are advanced), the array can be reset, and the process begun over again.

Note that because of the order of reading out rows 1 through N of array 40, the integration times of the rows are not uniform. Row 1 has the shortest integration time, while row N has the longest. (The timing pattern shown in FIG. 5 assumes that sensor elements 42 do not contain any internal charge storage structure, such as an additional capacitor, or an internal A/D converter, which would allow the integration times of all the rows to be equalized.) Since every cell 84 in memory 50 receives and sums signals from all the sensor elements in the corresponding column of array 40, however, the cumulative integration time is the same for all pixels scanned by camera 24.

Figure 6:
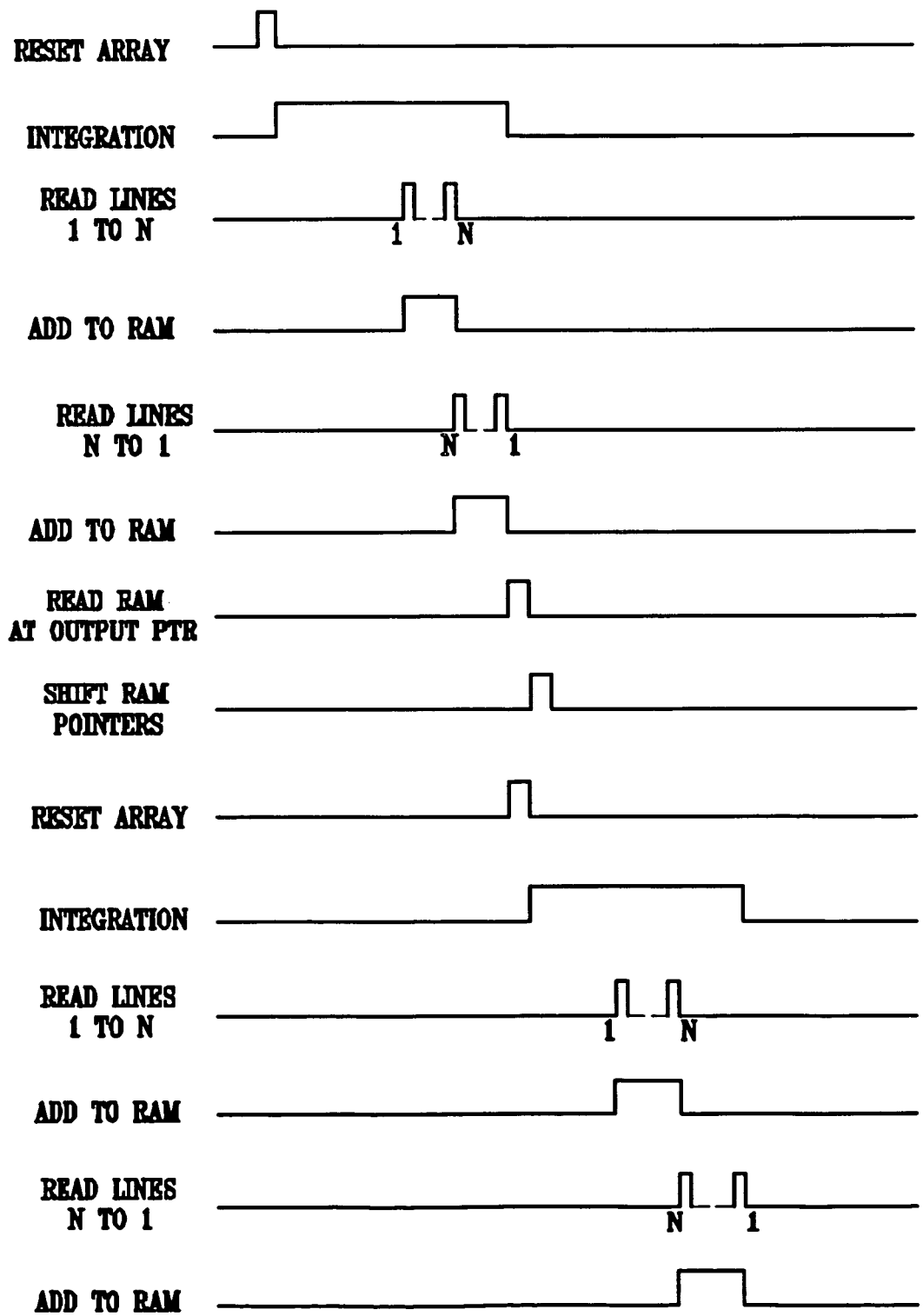

FIG. 6 is a timing diagram that schematically shows timing signals associated with the operation of imaging device 26, in accordance with another preferred embodiment of the present invention. This embodiment is similar to that shown in FIG. 5, except that now the signal from each sensor element 42 is read out of array 40 twice in each frame: once in forward sequential order from row 1 to N, and then again in reverse order from row N to 1. This approach is useful in achieving better uniformity of pixel response. The readout of sensor elements 42 is preferably non-destructive, i.e., the signal is read out of each sensor element without removing the charge from the element until the entire array is reset.

Figure 7:
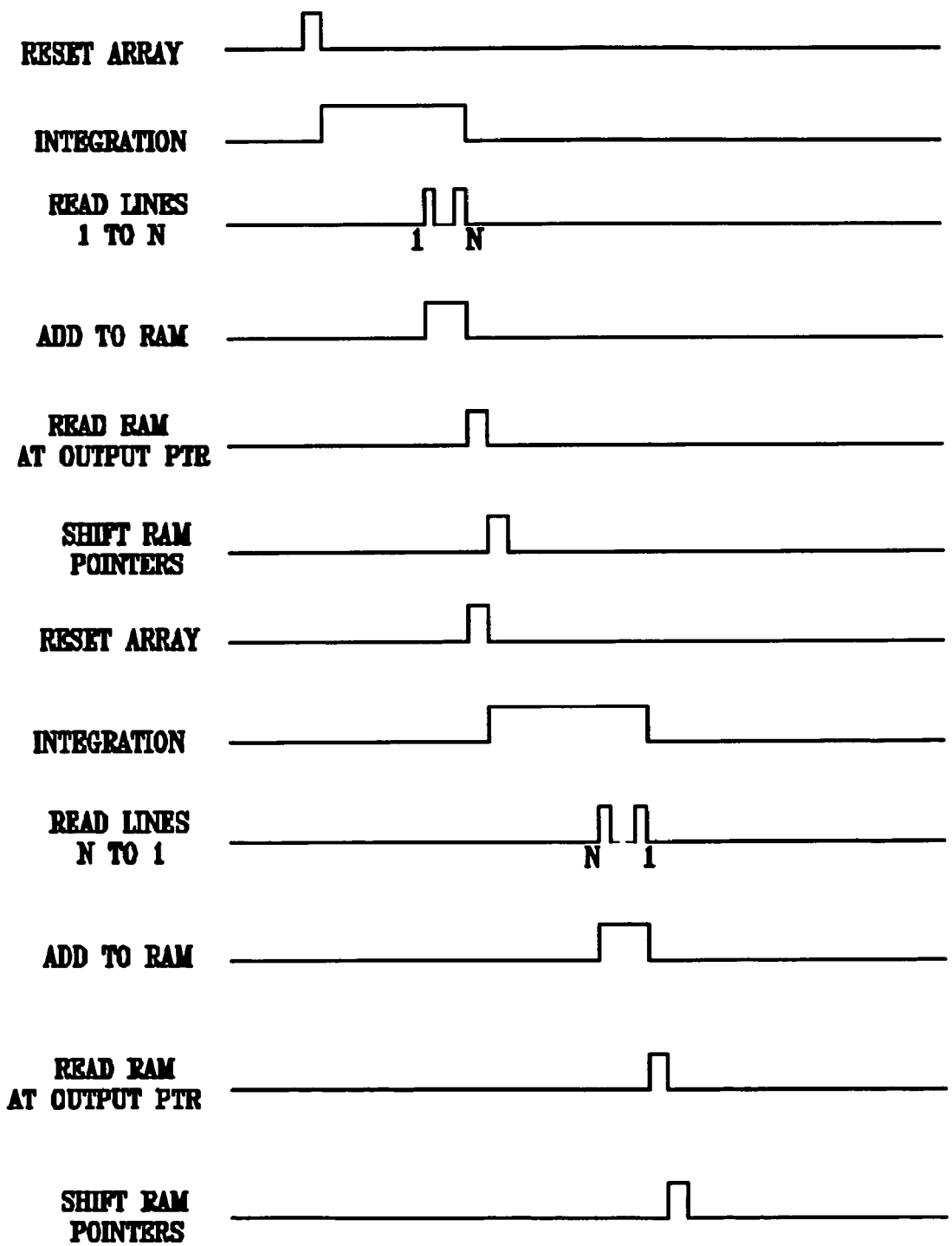

FIG. 7 is a timing diagram that schematically shows timing signals associated with the operation of imaging device 26, in accordance with yet another preferred embodiment of the present invention. Reading out each sensor element twice in each frame, as in the preceding embodiment, may reduce the speed of operation of device 26. Therefore, in the present embodiment, the direction of reading out the rows alternates from frame to frame: once from row 1 to N, and the next time from row N to 1. This approach provides improved pixel uniformity without compromising readout speed. Preferably, array 40 comprises an even number of rows, in order to ensure uniformity of response over all points on object 22.

Figure 8:
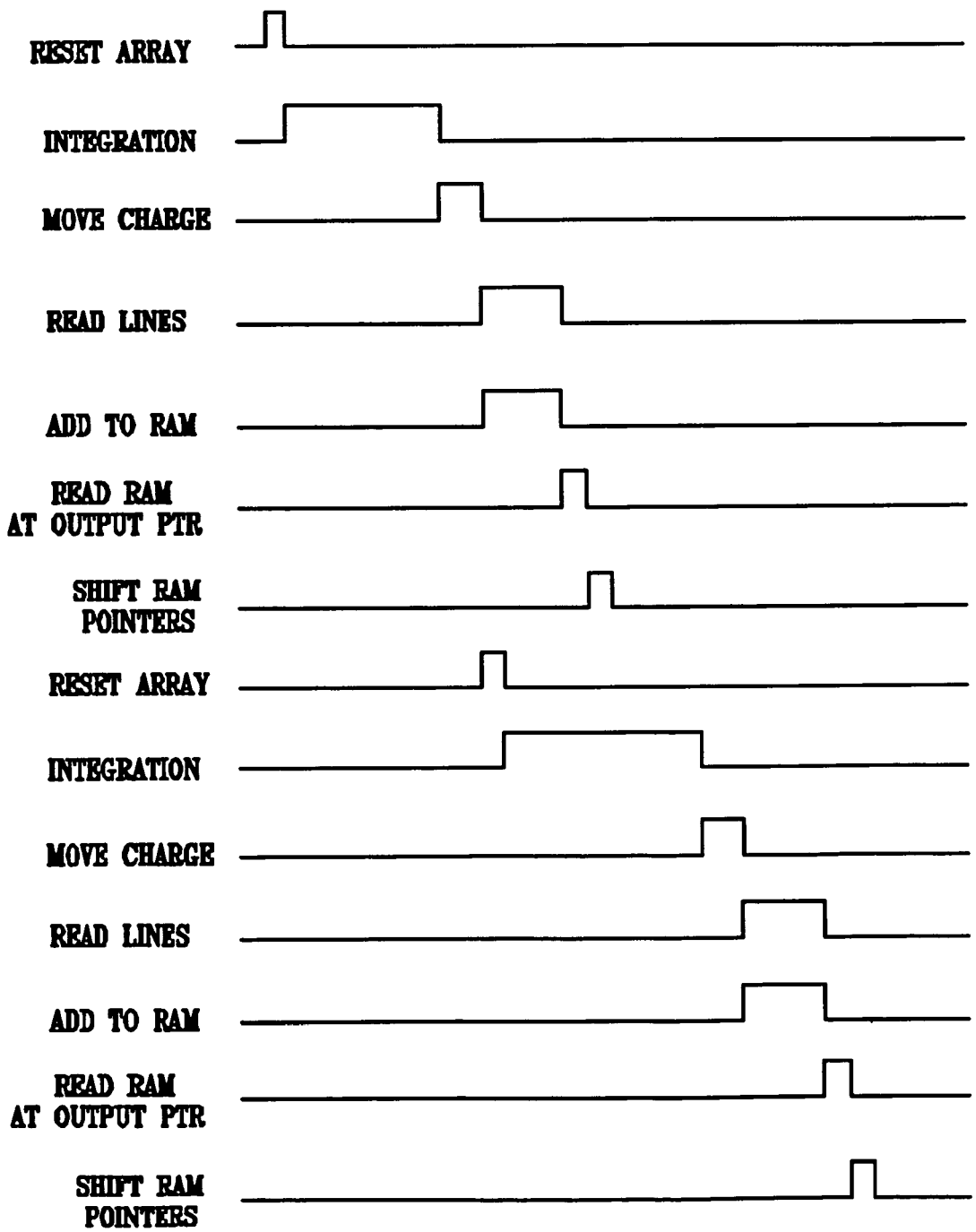

FIG. 8 is timing diagram that schematically shows timing signals associated with the operation of imaging device 26, in accordance with still another preferred embodiment of the present invention. In this embodiment, it is assumed that each sensor element in array 40 comprises a capacitor, memory cell or other internal component capable of storing its charge or signal value after integration is terminated. Thus, a uniform integration period can be set for all the elements of array 40. At the conclusion of the integration period, the charge accumulated by the photodetectors in all the sensor elements is transferred simultaneously to the respective internal storage components. The signals are then read out of the storage components, digitized (if necessary) and summed into memory 50 as described above. Meanwhile, the photodetectors are reset and begin their next integration period, while the processing of the signals from the preceding integration period is going on.

Although the embodiments described up to now are directed to monochrome imaging, system 20 and imaging device 26 may also be adapted to capture color images of board 22. One approach for this purpose would be to use colored strobe illumination (not shown), for example synchronized with the array clock, in which a different color light (typically red, green or blue) is used to illuminate the board in each successive frame, or for several successive frames. In order to generate color images, memory 50 must be divided into separate sections, for receiving and integrating the signals corresponding to the different colors. Within each section, the data are summed and read out using input and output pointers in substantially the same way as described above. As another alternative, described below with reference to the figures that follow, different color filters are applied to separate rows of array 40. Of course, different color filters may also be applied to separate columns of the sensor array, but this option may be less desirable as it necessarily detracts from the resolution of camera 24.

Figure 9A:
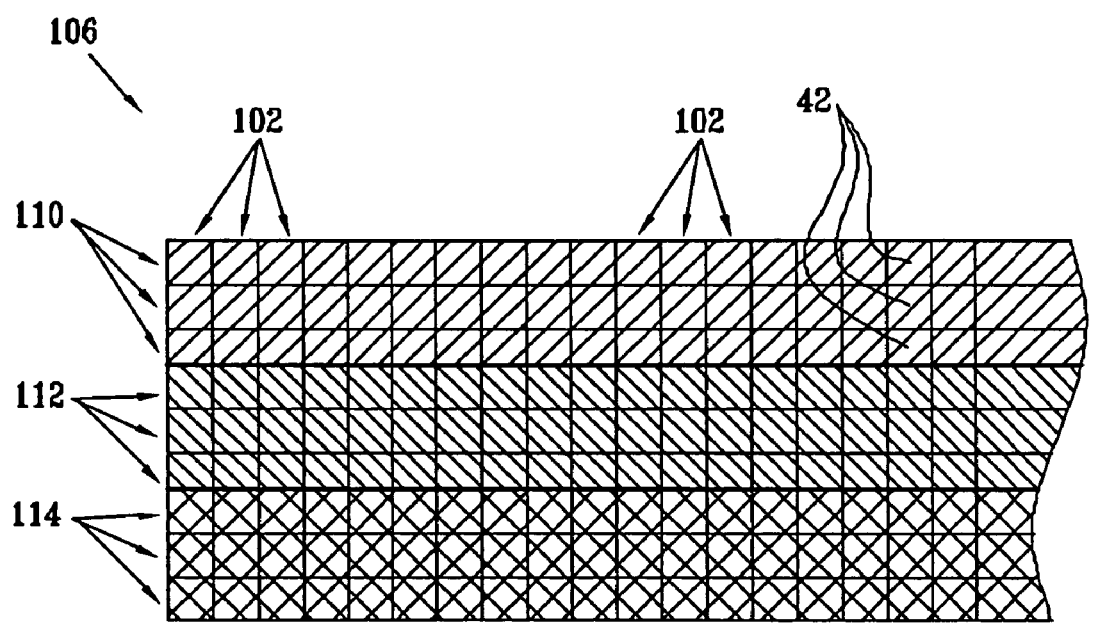
FIG. 9A is a block diagram that schematically illustrates a sensor array used in a two-dimensional scanning color imaging device, in accordance with a preferred embodiment of the present invention.

FIG. 9A is a block diagram that schematically illustrates a sensor array 106 used in a two dimensional scanning color imaging device, in accordance with a preferred embodiment of the present invention. This device is similar in most aspects to device 26, as shown and described above, and may be used in camera 24 in place of device 26. Therefore, only the salient differences, having to do specifically with capture of color images, are described here.

In the preferred embodiment seen in FIG. 9A, the rows of array 106 are divided into three groups: rows 110, which are configured to capture red light; rows 112, which are configured to capture green light; and rows 114, which are configured to capture blue light. Typically, each row or group of rows is overlaid by a suitable filter, which passes only the range of wavelengths that the particular row is supposed to detect, as is known in the art. Although each group of rows shown in FIG. 9A is shown as including three rows, each group may alternatively contain a larger or smaller number of rows. The number of rows need not be uniform among the different color groups. For example, a greater number of rows of one color (typically blue or green) can be used to compensate for non-uniform sensitivity of the silicon sensor and to provide enhanced resolution of the overall image. Other color schemes, having different number of groups or configured to capture different electromagnetic radiation wavelength, may also be used.

Figure 9B:
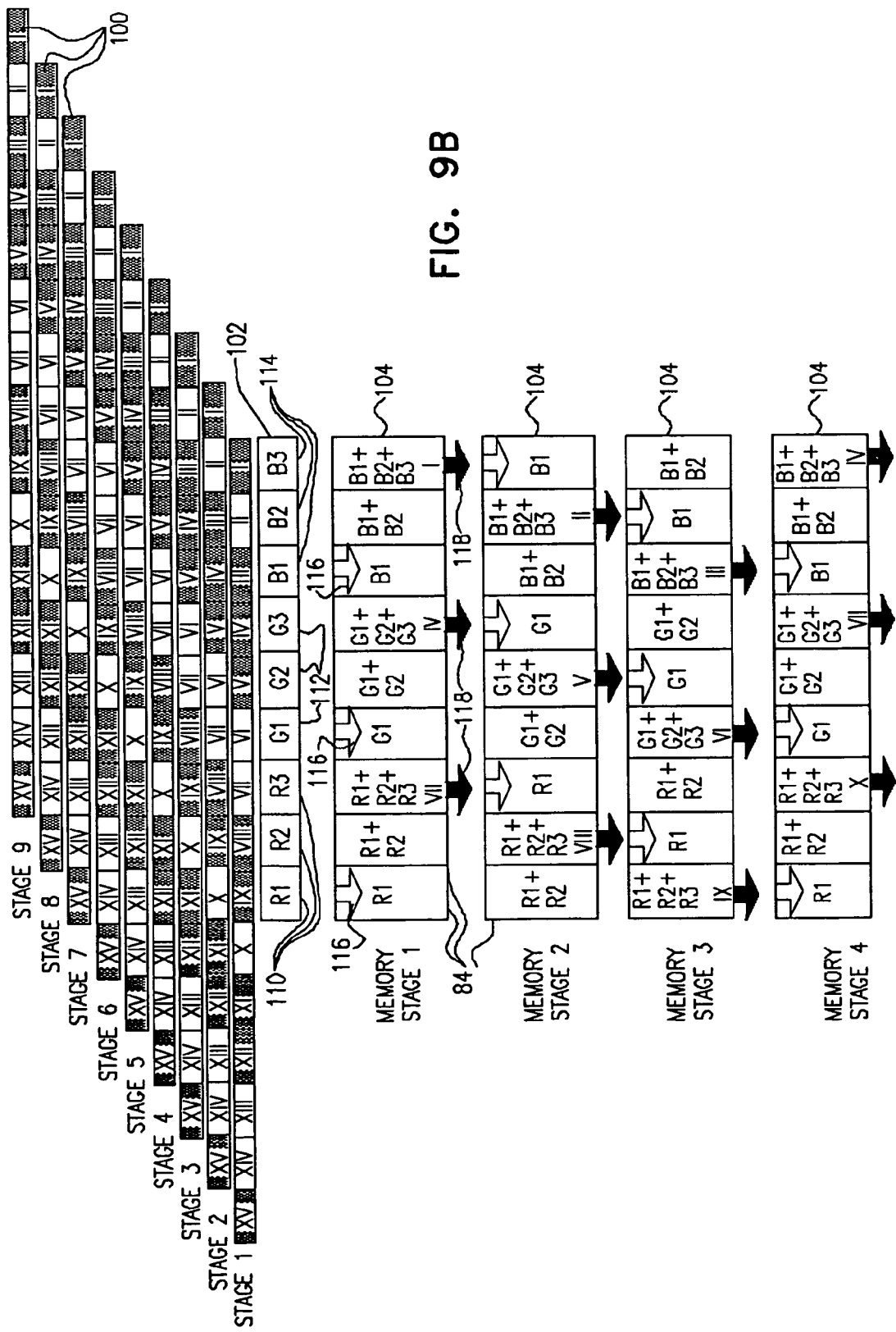
FIG. 9B is a block diagram that schematically shows details of detector elements and memory cells in the device of FIG. 9A, in accordance with a preferred embodiment of the present invention.

FIG. 9B is a block diagram that schematically shows details of sensor elements in one column 102 of array 106 and memory cells 84 in a corresponding column 104 in memory 50, illustrating imaging based on array 106, in accordance with a preferred embodiment of the present invention. At the top of the figure, object 100 is shown in each of nine successive positions relative to column 102, labeled stage 1 through stage 9, in a manner similar to that in which the successive object positions are shown above in FIG. 4. Each stage corresponds to a successive frame of array 106, i.e., to one cycle of the array clock. Object 100 is divided into pixels labeled I, II, III, . . . , XV, at a resolution corresponding to the resolution of array 106.

For each of stages I through IV, the figure shows the location of input pointers 116 and output pointers 118, along with the summed signals held in each memory cell 84. Three input pointers and three output pointers are provided, one for each color group. At each stage, the signals from the first red, green and blue pixels (R1, G1 and B1) are read into the memory cells indicated by the respective input pointers 116. The signals from the remaining pixels in each color group are summed into the next memory cells in column 104, in a manner similar to that shown in FIG. 4. In this way, after three frames are collected in the memory (i.e., three stages have passed), a given memory cell contains the sum of the signals from all three of the sensor elements in a given color group. This cell is indicated for readout by output pointer 118. Table I below lists the pixels whose color values are read out of column 104 at each stage:

TABLE I

PIXEL OUTPUT FOR FIG. 9B

| Stage | Red output | Green output | Blue output |
| --- | --- | --- | --- |
| 1 | VII | IV | I |
| 2 | VIII | V | II |
| 3 | IX | VI | III |
| 4 | X | VII | IV |
| 5 | XI | VIII | V |
| 6 | XII | IX | VI |
| 7 | XIII | X | VII |
| 8 | XIV | XI | VIII |
| 9 | XV | XII | IX |

It will be observed that the red, green and blue outputs generated by array 106 are out of registration by three rows (amounting to six rows between the red and the blue outputs). The registration can be easily corrected by adding a six-stage buffer for the red output and a three-stage buffer for the green output. These buffers can be provided in the two-dimensional color scanning imaging device itself or on a separate chip in camera 24. Alternatively, the registration adjustment may be performed by processor 34 without prior buffering.

Figure 10:
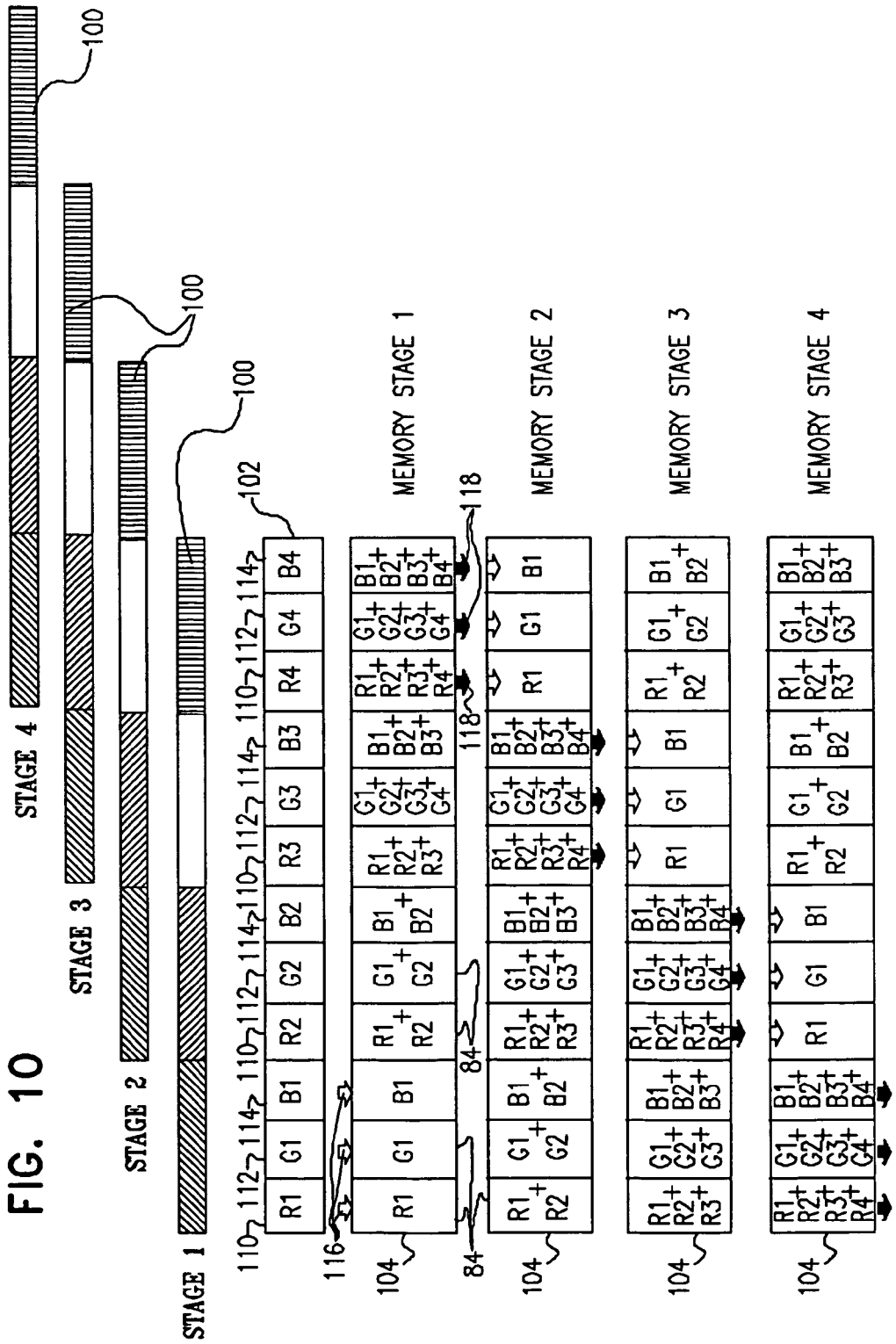
FIG. 10 is a block diagram that schematically illustrates detector elements and memory cells in a color two-dimensional imaging device, in accordance with another preferred embodiment of the present invention.

FIG. 10 is a block diagram showing detector elements and memory cells in a two-dimensional color scanning imaging device, in accordance with another preferred embodiment of the present invention. In this embodiment, red rows 110, green rows 112 and blue rows 114 are interleaved in cyclic alternation, i.e., RGB/RGB/RGB/RGB. Alternatively, other interleaving patterns may be used, such as RGBG/RGBG, etc. At each stage of operation of the device, each pixel on object 100 is imaged simultaneously by a sensor element in each of rows 110, 112 and 114. Therefore, the red, green and blue color images are mutually-registered without the need for buffering. The scanning of the imaging array over the object and the array clock are timed so that from each frame to the next, object 100 advances by a distance equivalent to one cyclic group of rows, i.e., by three sensor elements. As a result, a scanning system based on this embodiment will have high throughput but low resolution when compared to the embodiment of FIGS. 9A and 9B.

As in the preceding embodiment, three input pointers 116 are provided, indicating cells 84 to which the first red, green and blue sensor signals (R1, G1 and B1) are to be written at each stage. Three output pointers 118 indicate the cells from which the summed pixel values are to be read out. For the present embodiment, in which the RGB cycle repeats four times, the pointers return to their starting values after four frames, labeled stages 1, 2, 3 and 4, are completed.

Figure 11A:
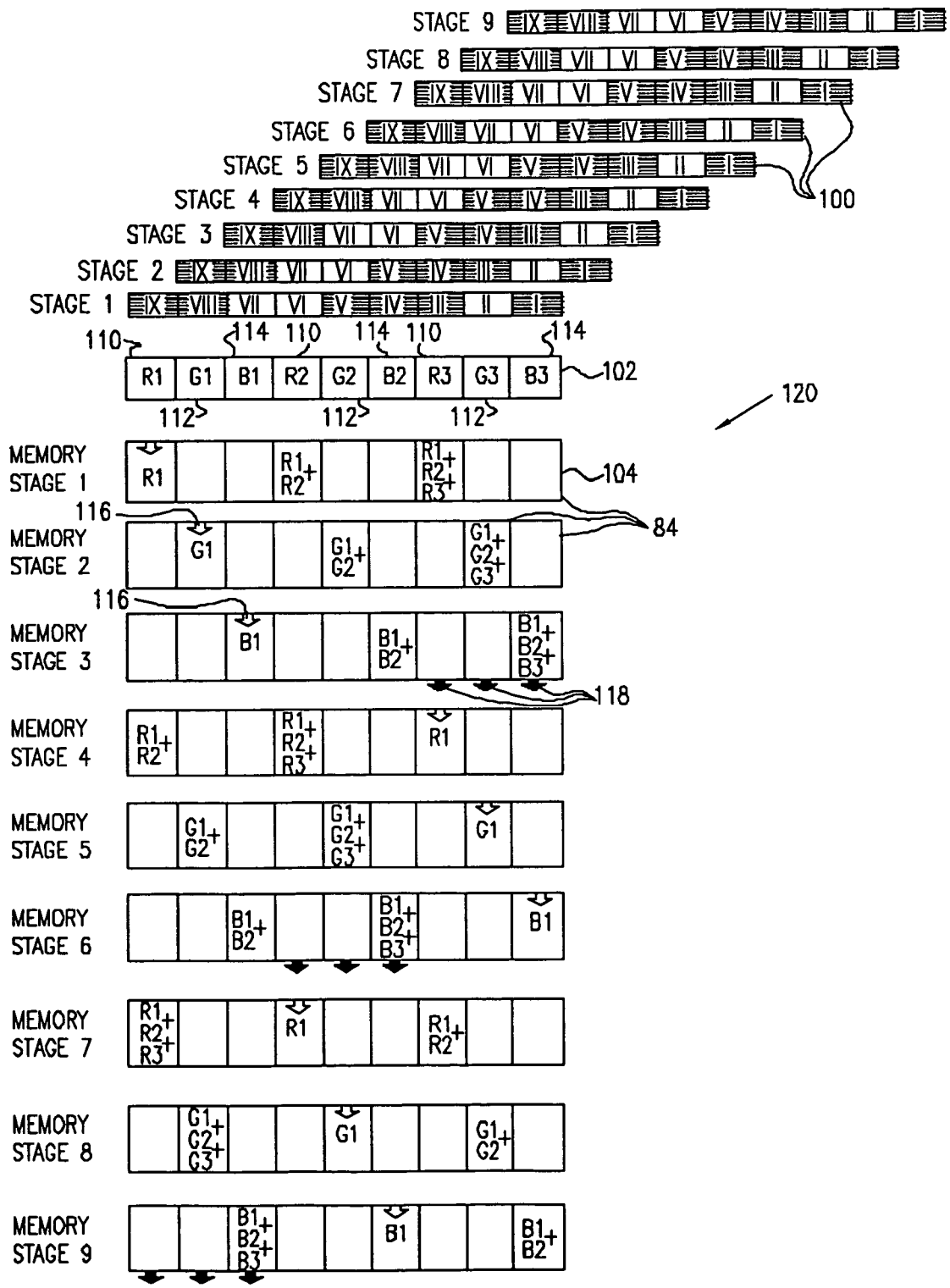
FIG. 11A is a block diagram that schematically illustrates detector elements and memory cells in a color two-dimensional imaging device, in accordance with still another preferred embodiment of the present invention.

FIGS. 11A, B and C are block diagrams that schematically illustrate detector elements and memory cells in a two-dimensional color scanning imaging device, in accordance with still another preferred embodiment of the present invention. Here, too, as in the preceding embodiment, red, green and blue rows of sensor elements are interleaved in the sensor array, and the output pixel values in all three colors are in mutual registration. In the present embodiment, however, full resolution is maintained, at the expense of reduced speed and increased memory size. An imaging device that is configured to operate in the manner shown in FIGS. 11A–C can be reprogrammed in software (or firmware) to operate in the mode of FIG. 10, as well, with higher throughput but reduced resolution.

The memory in the embodiment of FIGS. 11A–C comprises three columns 104 for each column 102 of the sensor array. Preferably, columns 104 are organized in three sections of memory cells 84: section 120 in FIG. 11A, section 122 in FIG. 11B and section 124 in FIG. 11C. The number of memory cells in each section is equal to the number of sensor elements in the sensor array. The columns of memory cells in each section are configured to collect and buffer the sensor signals from all three colors of every third pixel in object 100. Thus, in each successive stage, input pointers 116 for each color shift from one section to the next so that, for example, the signal from the first blue sensor element (B1) is fed to section 124 in stage 1, section 122 in stage 2, and section 120 in stage 3. These signal values belong respectively to pixel VII (stage 1), pixel VIII (stage 2) and pixel IX (stage 3). The signal values from the subsequent blue sensor elements (B2 and B3) are summed into the memory cells that are displaced by three and six cells, respectively, from the blue input pointer. The green and red signals are treated similarly. At each stage, one color is fed to each of the sections. According to this scheme, each of the memory cells is read from and written to only once in every three stages. During the other two stages, the cell simply holds its previous value. It is noted that only memory cells that are updated at the respective stage are shown, for clarity.

At each stage, output pointers 118 indicate three adjacent memory cells 84 to be read out from one of the three sections. The output pointers alternate from section to sections in each cycle. The three cells that are read out in each stage contain the red, green and blue pixel values, respectively, of one of the pixels, which are read out of the memory simultaneously. Since buffering is performed in the memory itself, no external buffering is required. Table II below lists the pixels whose values are read out at each stage:

TABLE II

PIXEL OUTPUT FOR FIG. 9B

| Stage | Pixel output | Read from memory section: |
|---|---|---|
| 1 | I | 124 |
| 2 | II | 122 |
| 3 | III | 120 |
| 4 | IV | 124 |
| 5 | V | 122 |
| 6 | VI | 120 |
| 7 | VII | 124 |
| 8 | VIII | 122 |
| 9 | IX | 120 |

Although the preferred embodiments described above relate particularly to detection of visible light, the principles of the present invention may similarly be adapted for detection of other types of radiation, and particularly for infrared and ultraviolet light. Thus, the "colors" mentioned above should be interpreted more generally as referring to different wavelength bands.

It will thus be appreciated that the preferred embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An inspection system comprising:
   an integrated circuit having formed thereon an at least one two dimensional array of photosensors and providing a plurality of pixelized images, each image representing a portion of an object to be inspected;
   a composite image generator digitally adding together corresponding pixels of said plurality of images and providing a composite image of said object to be inspected; and
   a defect analyzer operative to receive said composite image and to provide a defect report.

2. The inspection system claimed claim 1 and further comprising a scanner having a support assembly supporting said object to be inspected and wherein said integrated circuit is operative to acquire said plurality of images during scanning thereof.

3. The inspection system claimed in claim 1 and wherein said plurality of images comprises a plurality of digital images.

4. The inspection system claimed in claim 1 and wherein each image in said plurality of images at least partially overlaps another image in said plurality of images.

5. The inspection system claimed in claim 4 and wherein an overlap between a first image and a second image comprises at least half of said second image.

6. The inspection system claimed in claim 4 and wherein an overlap between a first image and a second image comprises all of said second image except for a single row of pixels output by said at least one two dimensional array of photosensors.

7. The inspection system claimed in claim 1 and further comprising an illumination assembly generally continuously illuminating said object to be inspected and wherein said integrated circuit is operative to acquire said plurality of images during illumination thereof.

8. The inspection system claimed in claim 1 and further comprising an illumination assembly generally non-continuously illuminating said object to be inspected, and wherein said integrated circuit is operative to acquire said plurality of images during non-continuous illumination thereof.

9. The inspection system claimed in claim 8 and wherein said illumination assembly is operative to provide said non-continuous illumination synchronously with said integrated circuit acquiring images of said object.

10. The inspection system claimed in claim 1 and wherein said integrated circuit has integrally formed thereon, in addition to said at least one two dimensional array of photosensors, at least one A/D converter receiving outputs from said at least one two dimensional array of photosensors.

11. The inspection system claimed in claim 10 and wherein said at least one A/D converter comprises an A/D converter associated with each photosensor in said array.

12. The inspection system claimed in claim 10 and wherein said at least one A/D converter comprises an A/D converter associated with a plurality of photosensors.

13. The inspection system claimed in claim 10 and wherein said CMOS integrated circuit has additionally integrally formed thereon a plurality of digital registers temporarily storing the outputs of said A/D converters.

14. The inspection system claimed in claim 13 and wherein said CMOS integrated circuit has additionally integrally formed thereon:
   a digital memory storing image data provided by said array; and
   a plurality of digital adders adding the outputs of said digital registers to corresponding image data stored in said digital memory.

15. The inspection system claimed in claim 14 and wherein said digital memory comprises an array of digital memory cells.

16. The inspection system claimed in claim 14 and wherein said CMOS integrated circuit comprises timing circuitry associated with said array, said adders and said digital memory, said timing circuitry generating a sequence of clock cycles.

17. The inspection system claimed in claim 16 and wherein said CMOS integrated circuit comprises:
   an input pointer indicating at each clock cycle a location in said digital memory at which to add an output of said at least one A/D converters; and
   an output pointer indicating at each clock cycle a location in said digital memory from which to retrieve said image data.

18. The inspection system claimed in claim 17 and wherein said clock is operative to change a location of said input pointer and to change a location of said output pointer at each clock cycle.

19. The inspection system claimed in claim 1 and wherein said integrated circuit is a CMOS integrated circuit.

20. The inspection system claimed in claim 1 and wherein said object is an electrical circuit.

21. A method for inspecting objects comprising:
   acquiring a plurality of substantially overlapping pixelized images each image representing a portion of an object to be inspected;
   digitally adding together corresponding pixels of said images to provide a composite image of said object; and analyzing said composite image to detect defects in said object.

22. The method claimed in claim 21 and wherein said acquiring comprises acquiring said images with a CMOS integrated circuit.

23. The method claimed in claim 21 and wherein said acquiring comprises acquiring images of an electrical circuit.

24. The method claimed in claim 21 and wherein said acquiring further comprises illuminating said object using generally continuous illumination.

25. The method claimed in claim 21 and wherein said acquiring further comprises:
   acquiring said images at a frame rate; and
   illuminating said object using generally non-continuous illumination fluctuating at a intensity fluctuation rate synchronized with said frame rate.

26. The method claimed in claim 21 and wherein said digitally adding comprises converting an image from an analog format to a digital format.

27. The method claimed in claim 26 and wherein said digitally adding comprises:
   retrieving a previously acquired image from a memory;
   digitally adding a portion of a newly acquired image in a digital format to a portion of said previously acquired image; and
   returning to memory an image resulting from said digitally adding a portion.

28. An imaging system comprising:
   an integrated circuit having formed thereon an at least one two dimensional array of photosensors and providing a plurality of pixelized images, each image representing a partially overlapping portion of an object to be imaged; and
   a composite image generator digitally adding together corresponding pixels of said plurality of images and providing a composite image of said object.

29. The imaging system claimed claim 28 and further comprising a scanner having a support assembly supporting said object to be inspected and wherein said integrated circuit is operative to acquire said plurality of images during scanning thereof.

30. The imaging system claimed in claim 28 and wherein said plurality of images comprises a plurality of digital images.

31. The imaging system claimed in claim 28 and wherein each image in said plurality of images at least partially overlaps another image in said plurality of images.

32. The imaging system claimed in claim 31 and wherein an overlap between a first image and a second image comprises at least half of said second image.

33. The imaging system claimed in claim 31 and wherein an overlap between a first image and a second image comprises all of said second image except for a single row of pixels output by said at least one two dimensional array of photosensors.

34. The imaging system claimed in claim 28 and further comprising an illumination assembly generally continuously illuminating said object to be imaged and wherein said integrated circuit is operative to acquire said plurality of images during illumination thereof.

35. The imaging system claimed in claim 28 and further comprising an illumination assembly generally non-continuously illuminating said object to be imaged, and wherein said integrated circuit is operative to acquire said plurality of images during non-continuous illumination thereof.

36. The imaging system claimed in claim 35 and wherein said illumination assembly is operative to provide said non-continuous illumination synchronously with said integrated circuit acquiring images of said object.

37. The imaging system claimed in claim 28 and wherein said integrated circuit has integrally formed thereon, in addition to said at least two dimensional array of photosensors, at least one A/D converter receiving outputs from said at least one two dimensional array of photosensors.

38. The imaging system claimed in claim 37 and wherein said at least one A/D converter comprises an A/D converter associated with each photosensor in said array.

39. The imaging system claimed in claim 37 and wherein said at least one A/D converter comprises an A/D converter associated with a plurality of photosensors.

40. The imaging system claimed in claim 37 and wherein said integrated circuit has additionally integrally formed thereon a plurality of digital registers temporarily storing the outputs of said A/D converters.

41. The imaging system claimed in claim 40 and wherein said integrated circuit has additionally integrally formed thereon:
   a digital memory storing image data provided by said array; and
   a plurality of digital adders adding the outputs of said digital registers to corresponding image data stored in said digital memory.

42. The imaging system claimed in claim 41 and wherein said digital memory comprises an array of digital memory cells.

43. The imaging system claimed in claim 41 and wherein said integrated circuit comprises timing circuitry associated with said array, said adders and said digital memory, said timing circuitry generating a sequence of clock cycles.

44. The imaging system claimed in claim 43 and wherein said integrated circuit comprises:
   an input pointer indicating at each clock cycle a location in said digital memory at which to add an output of said at least one A/D converters; and
   an output pointer indicating at each clock cycle a location in said digital memory from which to retrieve said image data.

45. The imaging system claimed in claim 44 and wherein said clock is operative to change a location of said input pointer and to change a location of said output pointer at each clock cycle.

46. The imaging system claimed in claim 28 and wherein said integrated circuit is a CMOS integrated circuit.

47. The imaging system claimed in claim 28 and wherein said object is an electrical circuit.

48. A method for imaging objects comprising:
   acquiring a plurality of substantially overlapping pixelized images each image representing a portion of an object to be imaged; and
   digitally adding together corresponding pixels of said images to provide a composite image of said object.

49. The method claimed in claim 48 and wherein said acquiring comprises scanning an at least one two dimensional array of photosensors relative to said object.

50. The method claimed in claim 49 and wherein said acquiring comprises acquiring said images using an at least one two dimensional array of photosensors disposed on a CMOS integrated circuit.

51. The method claimed in claim 48 and wherein said acquiring comprises acquiring said images using an at least one two dimensional array of photosensors disposed on a CMOS integrated circuit.

52. The method claimed in claim 48 and wherein said acquiring comprises acquiring images of an electrical circuit.

53. The method claimed in claim 48 and wherein said acquiring further comprises illuminating said object using generally continuous illumination.

54. The method claimed in claim 48 and wherein said acquiring further comprises:
   acquiring said images at a frame rate; and
   illuminating said object using generally non-continuous illumination fluctuating at an intensity fluctuation rate synchronized with said frame rate.

55. The method claimed in claim 48 and wherein said digitally adding comprises converting an image from an analog format to a digital format.

56. The method claimed in claim 55 and wherein said digitally adding comprises:
   retrieving a previously acquired image from a memory;
   digitally adding a portion of a newly acquired image in a digital format to a portion of said previously acquired image; and
   returning to memory an image resulting from said digitally adding a portion.

* * * * *